US009867585B2

(12) United States Patent
Scanlan et al.

(10) Patent No.: US 9,867,585 B2

(45) Date of Patent: Jan. 16, 2018

(54) METHOD FOR OPTIMALLY VISUALIZING A MORPHOLOGIC REGION OF INTEREST OF A BONE IN AN X-RAY IMAGE

(71) Applicants: Smith & Nephew, Inc., Memphis, TN (US); A2 Surgical, Le Mans (FR)

(72) Inventors: Sean Scanlan, Winchester, MA (US); Stéphane Lavallee, St. Martin d'Uriage (FR); Laurence Chabanas, Saint-Pierre-d'Allevard (FR); Asheesh Bedi, Ann Arbor, MI (US); Thomas Byrd, Nashville, TN (US); Bryan Kelly, Riverside, CT (US); Christopher Larson, Edina, MN (US)

(73) Assignees: Smith & Nephew, Inc., Memphis, TN (US); A2 Surgical (FR)

( * ) Notice: Subject to any disclaimer, the term of this patent is extended or adjusted under 35 U.S.C. 154(b) by 133 days.

(21) Appl. No.: 15/027,805

(22) PCT Filed: Oct. 8, 2014

(86) PCT No.: PCT/EP2014/071526

§ 371 (c)(1),
(2) Date: Apr. 7, 2016

(87) PCT Pub. No.: WO2015/052228

PCT Pub. Date: Apr. 16, 2015

(65) Prior Publication Data

US 2016/0235381 A1 Aug. 18, 2016

(30) Foreign Application Priority Data

Oct. 8, 2013 (EP) .................................... 13187728

(51) Int. Cl.

*G06K 9/00* (2006.01)
*A61B 6/00* (2006.01)

(Continued)

(52) U.S. Cl.

CPC .............. *A61B 6/505* (2013.01); *A61B 6/032* (2013.01); *A61B 6/463* (2013.01); *A61B 6/466* (2013.01);

(Continued)

(58) Field of Classification Search

None

See application file for complete search history.

(56) References Cited

U.S. PATENT DOCUMENTS

2015/0094564 A1 * 4/2015 Tashman ................ A61B 6/505 600/424

OTHER PUBLICATIONS

Harris, M.D. "The Geometry and Biomechanics of Normal and Pathomorphologic Human Hips", Aug. 1, 2013 (Aug. 1, 2013), Retrieved from the Internet: URL:http://mrl.sci.utah/edu/papers/MHarris_phd_dissertation_062013.pdf [retrieved on Apr. 30, 2014].

(Continued)

*Primary Examiner* — Atiba O Fitzpatrick

(74) *Attorney, Agent, or Firm* — Burns & Levinson LLP; Joseph M. Maraia

(57) ABSTRACT

The invention relates to a method for optimally visualizing a morphologic region of interest of a bone in an X-ray image of a patient, comprising: —receiving a set of 3D medical images of the bone, —creating a 3D bone model of at least part of the bone comprising said region of interest from said set of 3D images, —determining a criterion representative of a visualization of the extent of said morphologic region of interest, —automatically determining from the 3D bone model optimal relative bone and X-ray orientation so as to optimize said criterion for said patient, —creating at least one virtual X-ray image of the bone from said set of 3D images according to said optimal relative bone and virtual X-ray orientation.

10 Claims, 2 Drawing Sheets

M
∢ : 77°
C
N

(51) Int. Cl.
*A61B 6/03* (2006.01)
*G06F 19/00* (2011.01)
*G06T 7/00* (2017.01)
*G06T 7/11* (2017.01)

(52) U.S. Cl.
CPC ............ *A61B 6/467* (2013.01); *A61B 6/5217* (2013.01); *A61B 6/5223* (2013.01); *G06F 19/321* (2013.01); *G06F 19/3437* (2013.01); *G06T 7/0012* (2013.01); *G06T 7/11* (2017.01); *G06T 2207/10121* (2013.01); *G06T 2207/30008* (2013.01)

(56) References Cited

OTHER PUBLICATIONS

Milone, M.T. et al. "Novel CT-based Three-dimensional Software Improves the Characterization of Cam Morphology", Clinical Orthopaedics and Related Research, vol. 471, No. 8, Jan. 30, 2013 (Jan. 30, 2013), pp. 2484-2491.
Banerjee, P. et al. "Femoroacetabular impingement: a review of diagnosis and management", Current Reviews in Musculoskeletal Medicine, vol. 4, No. I, Mar. 1, 2011 (Mar. 1, 2011), pp. 23-32.
Yazdifar, M. et al. "Evaluation of Hip Impingement Kinematics on Range of Motion", Jul. 21, 2013 (Jul. 21, 2013), Human-Computer Interaction. Towards Intelligent and Implicit Interaction, Springer Berlin Heidelberg, Berlin, Heidelberg, pp. 262-269.
International Search Report dated Jan. 5, 2015 for PCT/EP2014/071526.

* cited by examiner

METHOD FOR OPTIMALLY VISUALIZING A MORPHOLOGIC REGION OF INTEREST OF A BONE IN AN X-RAY IMAGE

CROSS REFERENCE TO RELATED APPLICATIONS

This application is the U.S. national phase entry under 35 U.S.C. §371 of International Application No. PCT/EP2014/071526, filed Oct. 8, 2014, entitled METHOD FOR OPTIMALLY VISUALIZING A MORPHOLOGIC REGION OF INTEREST OF A BONE IN AN X-RAY IMAGE, which in turn claims priority to European Application No. 13187728.4, filed Oct. 8, 2013, which is incorporated herein by reference in its entirety for all purposes.

FIELD OF THE INVENTION

The invention relates to a method for optimally visualizing a morphologic region of interest of a bone in an X-ray image of a patient.

BACKGROUND OF THE INVENTION

When a morphologic region of interest of a bone has to be visualized in an X-ray image including said bone, the orientation of the bone in the image may not be optimal in view of assessing the whole extent of the region of interest.

Indeed, despite the fact that the radiologist or technician attempts to position the bone in an optimal position with regard to the X-ray orientation, the relative bone and X-ray orientation may be such that the region of interest is at least partially masked by another part of the bone and thus hinders a correct assessment of the bone morphology.

This issue arises in particular in—but not limited to—the assessment of femoro-acetabular impingement (FAI).

Femoroacetabular impingement is characterized by pathologic bony lesions on the acetabulum ("pincer" lesion) and/or femoral head-neck junction ("cam" lesion).

These bony lesions can cause intra and extra-articular collisions within the hip joint during certain dynamic activities, resulting in structural damage to the cartilage and labrum of the hip joint.

Bony lesions associated with FAI are typically treated with open or arthroscopic resection of the pathologic bony lesion.

The current standard of care relies on standard 2D X-ray views (such as AP (antero-posterior) pelvis, Dunn lateral, cross-leg lateral) and 3D medical imaging modalities (in particular CT (Computed Tomography) and MRI (Magnetic Resonance Imaging)) to perform a pre-operative assessment of the extent of the bony lesion associated to FAI and create a surgical resection plan.

When performing a pre-operative radiographic assessment, multiple 2D X-ray views are required in different hip joint positions and different X-ray orientation in an attempt to characterize the 3D nature of the bony lesion.

Up to five X-rays are usually obtained for diagnosis and surgical planning.

These X-rays are often repeated due to errors in patient positioning during image acquisition, which result in increasing the radiation exposure for the patient and for medical staff.

Besides, the positions of the bony lesions can vary substantially from patient to patient.

As a result, due to the 2D nature of X-ray projection imaging, the radiographic views often fail to capture the full extent of the bony lesion.

This problem has been partially addressed with the increased utilization of pre-operative 3D medical imaging (CT and/or MRI) for more comprehensive visualization and measurement of bony lesions associated with FAI.

Measurements are often made in multiple planes from these 3D images and these images are sometimes segmented to create 3D renderings of the joint morphology.

Combining the information derived from X-rays, MRI and/or CT, the surgeon is usually able to adequately appreciate the 3D nature of the bony pathology and create a pre-surgical resection plan.

However, while the move to 3D imaging has improved the ability to develop a pre-operative resection plan, intra-operative assessment of the surgical resection of the bony lesion still relies primarily on 2D X-ray imaging, using C-arm fluoroscopy.

Hence, the surgeon often spends a significant amount of operative time moving the hip joint through a range of motion in order to determine the radiographic view for optimal visualization of the bony lesion.

It is indeed difficult for the surgeon to translate the pre-operative morphologic assessment (either 2D or 3D) into the specific hip joint position and/or X-ray orientation required for optimal visualization of the bony lesion.

Alternatively, some surgeons may not perform a thorough intra-operative radiographic assessment, thereby often missing the full extent of the bony deformity.

Taken together, the lack of optimized intra-operative radiographic views of the bony deformity leads to increased operating time, increased radiation exposure for the patient and medical staff and/or incomplete resection of the bony lesion.

BRIEF DESCRIPTION OF THE INVENTION

A goal of the invention is thus to overcome the above-mentioned problems and to provide a method for providing a patient-specific optimal visualization of a morphologic region of interest of a bone in an X-ray image.

The invention provides a method for optimally visualizing a morphologic region of interest of a bone in an X-ray image of a patient, comprising:

- receiving a set of 3D medical images of the patient's bone,
- creating a 3D bone model of at least part of the bone comprising said region of interest from said set of 3D images,
- determining a criterion representative of a visualization of the extent of said morphologic region of interest,
- automatically determining from the 3D bone model optimal relative bone and X-ray orientation so as to optimize said criterion for said patient,
- creating at least one virtual X-ray image of the bone from said set of 3D images according to said optimal relative bone and virtual X-ray orientation.

According to a preferred embodiment, said method comprises creating the at least one virtual X-ray image by projecting 3D bone voxel density of the set of 3D images according to said optimal relative orientation.

The morphologic region of interest may comprise a bone deformity, an implant and/or a fracture.

According to an embodiment, the bone is a femur and the morphologic region of interest comprises a femoral neck deformity responsible for cam type femoro acetabular impingement.

The method may further comprise computing and displaying a virtual resection of the bone onto the 3D bone model to simulate correction of a bone deformity.

According to an embodiment, the bone forms part of a joint and the set of 3D medical images comprises 3D images of the joint, the method then comprising:

- creating a 3D bone model of at least part of each bone of the joint including the morphologic region of interest from said set of 3D images,
- assigning to the bone joint a kinematic joint model, that may be selected from a database of kinematic joint models,
- automatically determining from the 3D bone model optimal relative bone and X-ray orientation in accordance with the kinematic joint model so as to optimize said criterion.

The kinematic joint model is for example a ball-and-socket model.

In the case of cam type femoro acetabular impingement, the criterion is the alpha angle defined as the angle between the hemi-line from the femoral sphere center in the direction of the neck axis and the radius from femoral sphere center and a point of the femoral head-neck junction, and optimizing the criterion comprises determining the maximum alpha angle.

The method then comprises determining a radius connecting the femoral head center and the point of the circumference of the femoral head-neck junction where said alpha angle is maximum, wherein optimal relative bone and X-ray orientation is obtained when the plane defined by the maximum alpha angle radius and the femoral neck axis is perpendicular to the X-ray orientation.

The set of 3D images can comprise CT images, MR images and/or ultrasound images.

Another aspect of the invention is a computer program product comprising computer-readable instructions which, when loaded and executed on a suitable system, perform the steps of the method described above.

Another object of the invention is a method of intra-operative X-ray imaging of a morphologic region of interest of a bone of a patient, wherein:

- patient-specific optimal relative bone and X-ray orientation is determined by the method as described above, and
- X-ray imaging is carried out in accordance with said optimal relative bone and X-ray orientation.

BRIEF DESCRIPTION OF THE DRAWINGS

Other features and advantages of the invention will be apparent from the detailed description that follows, based on appended drawings, wherein.

DETAILED DESCRIPTION OF THE INVENTION

Figure 1:
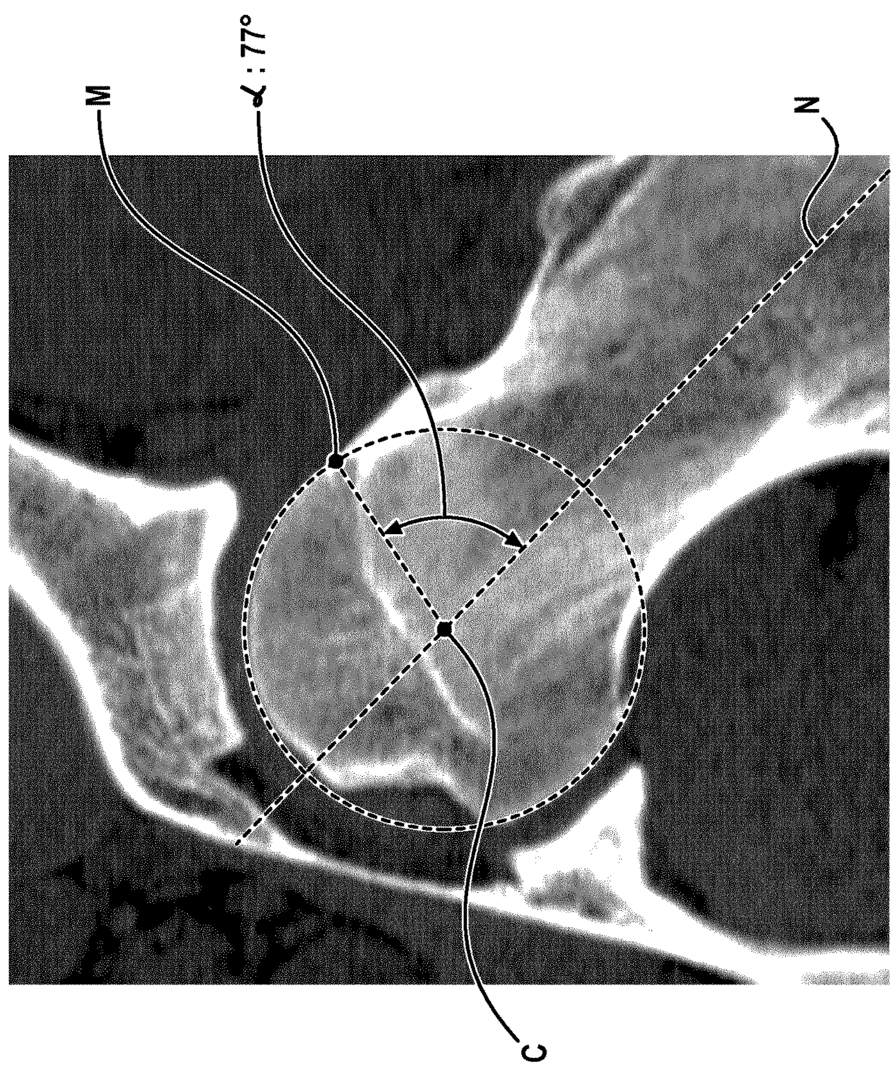
FIG. 1 illustrates the calculation of the alpha angle on the femoral head-neck junction in a 2D radial slice.

The detailed description that follows is focused on the hip joint, and more specifically on the femur, in view of optimally visualizing a deformity of the femoral head-neck junction of a specific patient, which may cause cam femoro-acetabular impingement.

However, the invention is not limited to this specific application but applies more generally to any bone having a morphologic region of interest to be visualized.

For example, such a morphologic region of interest can be a fracture to be reduced, an implant and/or a bone deformity.

Besides, other joints than the hip joint can be concerned by the invention, e.g. the knee, the ankle or the shoulder.

In other words, the invention can be used in the context of any surgical intervention that can benefit from optimal patient-specific radiographic views.

The method is carried out in a system comprising a computer and a screen for displaying a virtual radiographic image of the patient showing optimally the region of interest.

A software can be implemented on the computer to carry out the method.

The system also comprises a graphical user interface (GUI) that provides an interaction between a user and the software.

The graphical user interface may be displayed on the above-mentioned screen.

The method is based on 3D medical images of a bone of a patient having a region of interest to be visualized.

Said 3D medical images may have been acquired previously by CT, MRI and/or ultrasound and stored on a suitable medium so as to be able to be loaded upon request by the user.

In the case of femoro-acetabular impingement, the 3D medical images comprise images of the hip.

First, a 3D model of the acetabulum and the proximal femur comprising the head-neck junction is carried out from the 3D images.

Said 3D bone model can be obtained from an automatic segmentation of the 3D images.

Next, anatomical landmarks of the hip joint can be computed automatically and/or with manual methods.

The identified anatomical landmarks of the hip joint are used to define axes and an origin, forming an anatomic coordinate system.

According to an advantageous embodiment, a best-fit sphere is calculated to determine the femoral head anatomical landmarks.

The center of the best-fit sphere may then be considered to be the center of the femoral head.

There are several methods for computing the best-fit sphere to the femoral head. One example of a method for determining the best-fit sphere is to apply a robust least-square fitting of a sphere to a set of 3D points representing the cortical surface of the femoral head.

Optionally, the best-fit sphere to the femoral head can be determined by manual fitting of circles to the femoral head in at least two orthogonal 2D reformatted medical images.

Additional femoral landmarks can also be identified to create the femoral anatomic coordinate system. There are several methods for determining the medial-lateral axis of the femur. In one example, a medial-lateral axis of the femur is defined as the line joining the most posterior points of the distal femoral condyles.

Optionally, the medial-lateral axis of the femur can be defined using the transepicondyle axis of the distal femur.

The center of the distal femur is often used with the center of the femoral head to create a superior-inferior axis of the femur.

Next, a medial-lateral axis of the pelvis is then determined.

There are several methods for determining a medial-lateral axis of the pelvis. In one example, a medial-lateral axis of the pelvis is defined as the line joining the femoral head centers.

Optionally, the medial-lateral axis of the pelvis can be defined by the line joining the acetabular centers, where the acetabular centers are defined by fitting a sphere to the articulating surface of the acetabulum or by calculating the centroid of the set of 3D points representing the acetabular rim.

An additional option for determining the medial-lateral axis of the pelvis is to use the vector normal to a plane fit to the set of 3D points representing the acetabular rim.

The pelvic coordinate system can also be created using the anterior superior iliac spines and pubic symphysis to create the anterior pelvic plane.

Once coordinate systems are created, a kinematic model of the hip joint is advantageously defined to characterize the articulation of the hip.

According to an embodiment, the model is a ball joint model.

Alternatively, a more complex kinematic model of the joint can be used, including not only joint rotations but also translations.

However, the method can also be carried out based on the 3D model of the bone of interest alone, without taking into account the kinematics of the joint.

In the case of cam FAI, a widely used parameter to characterize the deformity is the alpha angle [Nötzli et al.].

Conventionally, the alpha angle is defined as the angle $\alpha$ between the hemi-line CN from the femoral sphere center C in the direction of the neck axis and the radius CM from femoral sphere center C and a point M of the femoral head-neck junction (see FIG. 1).

The alpha angle is calculated on 2D radial slices from the set of 3D images, at each position around a clockface referential of the femur.

A radius, called "maximum alpha angle radius", is determined that connects the femoral head center to the point along the circumference of the femoral head-neck junction where the maximum alpha angle is measured.

The optimal relative orientation of the femur and the X-ray is then obtained when the plane defined by said maximum alpha angle radius and femoral neck axis is normal to a virtual AP pelvic X-ray trajectory.

In such case, the bone deformity will be visualized in its full extent.

Since the maximum alpha angle radius may vary from a patient to another patient, this optimal relative orientation is specific to the patient.

Of course, the alpha angle is only an example of a criterion representative of the extent of the head-neck junction deformity, but other criteria may be applied depending on the kind of morphologic region of interest.

To define the optimal joint position, only the hip flexion and internal/external rotation angles may be used, adduction/abduction being minimized or set to zero.

This provides easier translation to the operating room environment, since modifying three degrees of freedom in the operating room is difficult.

Figure 2:
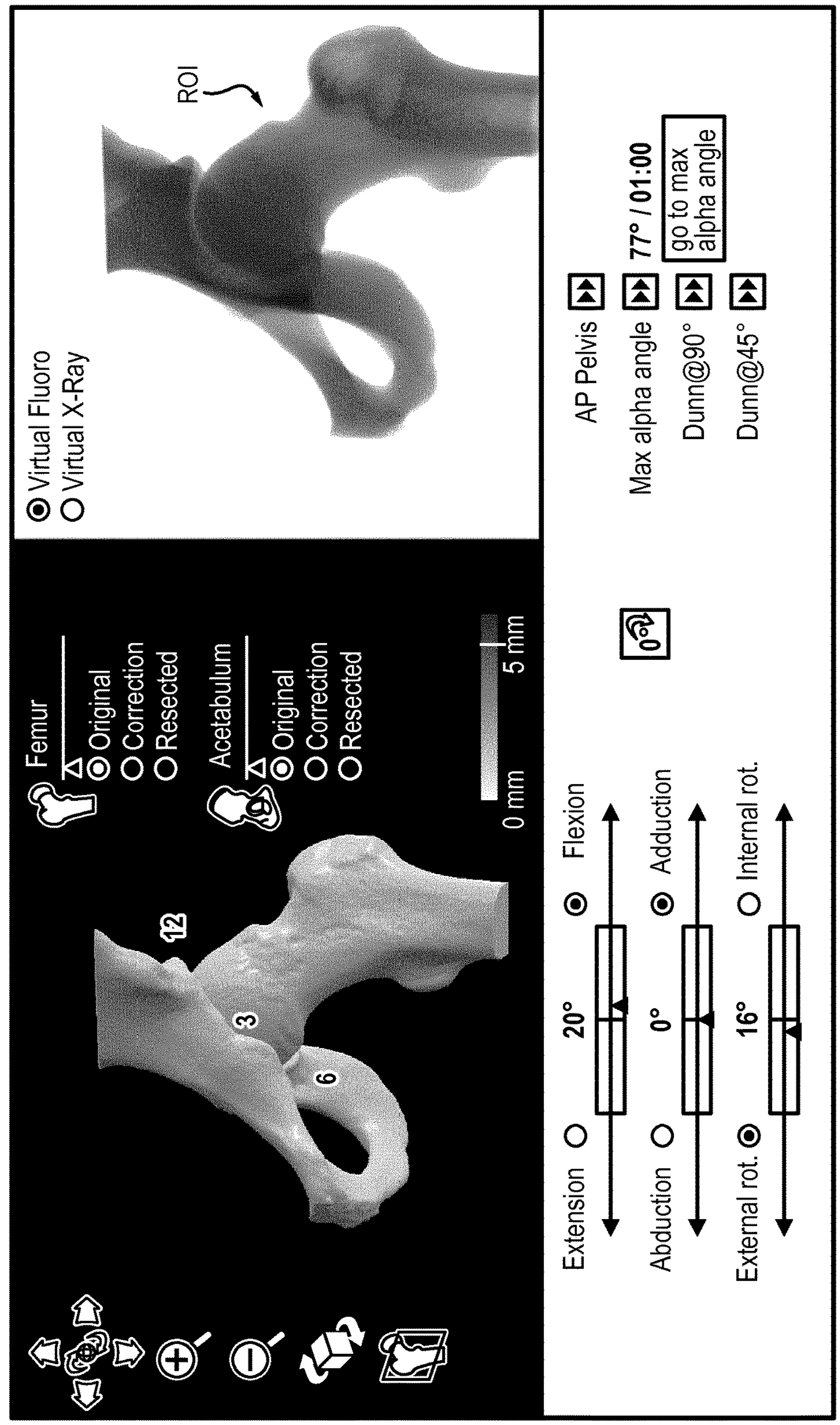
FIG. 2 shows a display of a 3D model of the hip (left) and a virtual 2D X-ray image (right) optimized for visualization of the maximum alpha angle according to an embodiment of the invention.

In practice, as shown in FIG. 2, a joint position of 20° of flexion and 16° of external rotation is recommended for visualization of the maximum alpha angle, which occurs at the 1:00 position on the femoral head-neck junction.

However, other parameters of the joint position can be chosen by the practitioner without departing from the scope of the invention.

As mentioned above, the optimal relative orientation that is determined is specific to the patient, since the optimized criterion is computed from a 3D surface model of the patient.

Once the optimal bone (or joint) position is defined, the software creates and displays virtual radiographic images of the bone morphology.

Said virtual X-ray image can be created from the 3D bone model by projecting 3D bone voxel density of the 3D images according to the above-determined patient-specific optimal relative orientation.

This technique is called "Digitally Reconstructed Radiograph" (DRR), which is well known in the field of image processing.

By proactively predicting an optimal orientation specific to the patient, the invention overcomes the limitations of standard X-ray views, where it is unknown whether one of the standard X-ray views is actually optimally capturing the bony pathology of the patient. In this regard, it is to be noted that the study reported in [Harris] retrospectively analyzes a population of patients with standard radiographic views and then determines the best of these standard views for capturing the maximum deformity on average for that population; however, this method does not allow knowing whether any of the standard views are truly optimal for a given patient.

The calculation of the optimal radiographic image can be performed in different ways.

According to an embodiment, the X-ray orientation is varied keeping the joint position constant.

According to another embodiment, the joint position is varied keeping the X-ray orientation constant.

According to an embodiment, the calculation determines both the joint position and the X-ray orientation for optimal radiographic view of the region of interest.

Different algorithms may be used for calculating the optimal radiographic view.

For instance, the variables can be varied parametrically or various optimization algorithms can be implemented.

One such optimization method could be based on a cost function that minimizes the total joint excursion (sum of three joint angles) while constraining the joint to physiologic motion and/or constraining the X-ray orientation to clinically-relevant orientations.

The practitioner can then output the optimal relative orientation of the bone and the X-ray, and/or print the virtual radiographic image for reference.

In view of carrying out additional X-ray imaging, the practitioner can use the previously determined patient-specific optimal relative orientation and position the patient and/or the X-ray imaging device so as to conform to this optimal relative orientation.

FIG. 2 shows a display, on the graphical user interface, of a 3D model of the hip (left) and a virtual 2D X-ray image (right) optimized for visualization of the maximum alpha angle according to an embodiment of the invention.

References 3, 6 and 12 on the 3D hip model represent respectively the 12 o'clock, 3 o'clock and 6 o'clock positions on the clockface referential of the femur.

The graphical user interface comprises three cursors to set or display the extension/flexion, abduction/adduction and external/internal rotation angles used to position the joint for generation of the virtual X-ray image.

In the embodiment shown here, the abduction/adduction is set to zero whereas the flexion angle is of 20° and the external rotation angle is of 16°.

On the virtual X-ray image, the deformity of the head-neck junction is designated by reference ROI.

When the morphologic region of interest is a bony deformity that has to be corrected, the software may compute a virtual resection of the bone and display it on the 3D model.

In conclusion, the invention is able to create a patient-specific optimal radiographic view of a morphologic region of interest of a bone from 3D morphologic models of the patient created from 3D imaging modalities.

The determination of optimal relative bone and X-ray orientation allows reducing the number of pre-operative X-rays and intra-operative fluoroscopic views required to properly visualize a patient-specific region of interest of a bone, such as a bone deformity associated with FAI.

Calculating virtual X-ray images eliminates the need for additional X-ray images in many cases, thereby reducing the radiation dose to which the patent is exposed and potentially avoiding patient positioning errors during X-ray acquisition.

Besides, the information obtained by calculating the optimal relative bone and X-ray orientation can be easily translated to the operating room to guide a surgeon in the positioning of the patient's joint and/or fluoroscopic trajectory.

The invention thus potentially reduces radiation dose, reduce operation time and also generates better images for visualization of the region of interest, leading to better patient outcomes.

REFERENCES

[Nötzli et al.] HP Nötzli, T F Wyss, C H Stoecklin, M R Schmid, K Treiber, J Hodler, The contour of the femoral head-neck junction as a predictor for the risk of anterior impingement, J Bone Joint Surg [Br], 84(4):556-60, 2002

[Harris] Michael Dennison Harris, The geometry and biomechanics of normal and pathomorphologic human hips, Dissertation submitted to the faculty of the University of Utah, Chapter 4, August 2013

The invention claimed is:

1. Method for optimally visualizing a morphologic region of interest of a bone in an X-ray image of a patient, comprising:

receiving a set of 3D medical images of the patient's bone, creating a 3D bone model of at least part of the bone comprising said region of interest from said set of 3D images, determining a criterion representative of a visualization of an extent of said morphologic region of interest, automatically determining from the 3D bone model optimal relative bone and X-ray orientation so as to optimize said criterion for said patient, and creating at least one virtual X-ray image of the bone from said set of 3D images according to said optimal relative bone and virtual X-ray orientation;

wherein the bone forms part of a joint and the set of 3D medical images comprises 3D images of the joint, and wherein the method further comprises:

creating the 3D bone model of at least part of each bone of the joint including the morphologic region of interest from said set of 3D images, assigning to the bone joint a kinematic joint model, and automatically determining from the 3D bone model optimal relative bone and X-ray orientation in accordance with the kinematic joint model so as to optimize said criterion;

wherein the bone is a femur and the criterion is an alpha angle defined as an angle between a hemi-line from a femoral sphere center in a direction of a femoral neck axis and a radius from the femoral sphere center and a point of a circumference of a femoral head-neck junction, and wherein optimizing the criterion comprises determining a maximum alpha angle.

2. Method according to claim 1, comprising creating the at least one virtual X-ray image by projecting 3D bone voxel density of the set of 3D images according to said optimal relative orientation.

3. Method according to claim 1, wherein the morphologic region of interest comprises a bone deformity, an implant and/or a fracture.

4. Method according to claim 1, wherein the morphologic region of interest comprises a femoral neck deformity responsible for cam type femoro acetabular impingement.

5. Method according to claim 3, comprising computing and displaying a virtual resection of the bone onto the 3D bone model to simulate correction of the bone deformity.

6. Method according to claim 1, wherein the kinematic joint model is a ball-and-socket model.

7. Method according to claim 1, comprising determining the radius from the femoral sphere center and the point of the circumference of the femoral head-neck junction where said alpha angle is maximum, wherein optimal relative bone and X-ray orientation is obtained when a plane defined by a maximum alpha angle radius and the femoral neck axis is perpendicular to the X-ray orientation.

8. Method according to claim 1, wherein the set of 3D images comprises CT images, MR images and/or ultrasound images.

9. One or more processors and one or more non-transitory computer usable medium that has computer readable code embodied therein, which, when loaded and executed by the one or more processors, perform the steps of the method according to claim 1.

10. Method of intra-operative X-ray imaging of a morphologic region of interest of a bone of a patient, wherein patient-specific optimal relative bone and X-ray orientation is determined by the method according to claim 1, and X-ray imaging is carried out in accordance with said optimal relative bone and X-ray orientation.

* * * * *